United States Patent [19]

Renger

[11] Patent Number: 5,493,100
[45] Date of Patent: Feb. 20, 1996

[54] THERMISTOR FLOW SENSOR AND RELATED METHOD

[75] Inventor: Herman L. Renger, Calabasas, Calif.

[73] Assignee: Pacesetter, Inc., Sylmar, Calif.

[21] Appl. No.: 365,271

[22] Filed: Dec. 28, 1994

[51] Int. Cl.[6] .............................. H05B 1/02; G01F 1/68; A61B 5/02
[52] U.S. Cl. .................... 219/497; 219/501; 219/505; 219/504; 73/204.19; 73/204.18; 73/204.14; 604/246; 374/39; 128/692
[58] Field of Search ..................... 219/497, 499, 219/501, 504, 505, 508, 494, 496; 73/204.13, 204.14, 204.15, 204.16, 204.17, 204.19, 25.03, 118.2; 604/246, 151–153; 374/39–41; 128/692, 691

[56] References Cited

U.S. PATENT DOCUMENTS

| | | | |
|---|---|---|---|
| 2,580,182 | 12/1951 | Morgan et al. | 73/154 |
| 3,372,590 | 3/1968 | Sterling | 73/204 |
| 3,719,083 | 3/1973 | Morris et al. | 73/204 |
| 4,501,145 | 2/1985 | Boegli et al. | 73/204 |
| 4,576,182 | 3/1986 | Normann | 128/692 |
| 4,627,840 | 12/1986 | Cuadra et al. | 604/151 |
| 4,848,147 | 7/1989 | Bailey et al. | 73/204.17 |
| 5,038,304 | 8/1991 | Bonne | 364/571.01 |
| 5,111,692 | 5/1992 | McQueen et al. | 73/295 |
| 5,119,674 | 6/1992 | Nielsen | 73/204.24 |
| 5,359,891 | 11/1994 | Yamamoto | 73/204.15 |

*Primary Examiner*—Mark H. Paschall
*Attorney, Agent, or Firm*—Lisa P. Weinberg

[57] ABSTRACT

A fluid flow rate measuring apparatus having a thermistor exposed to a flow of fluid and a driver circuit operable in an initial constant-voltage mode, in which it applies a substantially constant voltage across the thermistor, and a subsequent constant-current mode, in which it applies a substantially constant current through the thermistor, such current corresponding to the current level at the end of the constant-voltage mode. A voltage sensor measures the resultant voltage drop across the thermistor, which is a direct measurement of the fluid flow rate and which is substantially insensitive to variations in ambient temperature.

12 Claims, 2 Drawing Sheets

THERMISTOR FLOW SENSOR AND RELATED METHOD

BACKGROUND OF THE INVENTION

This invention relates generally to fluid flow sensors and, more particularly, to fluid flow sensors that incorporate a thermistor.

Fluid flow sensors of this particular kind are useful in conjunction with implantable devices such as cardiac pacemakers. Such devices typically now have the capability of monitoring numerous physical parameters of a patient's cardiac and circulatory systems, so as to detect and evaluate certain physiological problems and conditions. In addition to blood flow rate, the parameters that are monitored can include, for example, pulse rate, body temperature, and blood pressure. Based on its evaluation of these parameters, the pacemaker can execute any of numerous functions so as to correct for the problem or condition.

Blood flow rate sensors of this kind typically have included a thermistor implanted within a blood vessel and exposed to the flow of blood. A driver circuit directs an electrical current through the thermistor, which heats the thermistor and thereby causes its resistance to vary accordingly. The flow of blood past the thermistor carries heat energy away, thus reducing the amount of temperature increase. The amount of temperature increase thus varies with flow rate, with a maximum amount of temperature increase occurring for a flow rate of zero. The driver circuit monitors the rate of change of the thermistor's resistance, e.g., by monitoring the voltage drop across the thermistor while a constant current is applied, and it estimates the blood's flow rate accordingly.

One drawback to such prior blood flow rate sensors is that changes in ambient temperature, i.e., blood temperature, can affect the accuracy of the flow rate measurement. The ambient temperature affects the amount of heat the blood draws away from the thermistor, thus causing the thermistor's temperature to vary not only with flow rate but also with the ambient temperature. It should, therefore, be appreciated that there is a need for a flow rate measuring apparatus that provides an accurate measure of flow rate without being affected by ambient temperature. The present invention satisfies this need.

SUMMARY OF THE INVENTION

The present invention resides in an improved thermistor-based apparatus, and related method, for measuring fluid flow rate that is substantially insensitive to any variations in the fluid's ambient temperature. The apparatus includes a thermistor exposed to a flow of fluid and a driver circuit operable in two modes, including an initial constant-voltage mode and a subsequent constant-current mode. In the initial constant-voltage mode, the driver circuit applies a prescribed substantially constant voltage across the thermistor, to produce an electrical current that varies according to the thermistor's temperature. In the subsequent constant-current mode, the driver circuit applies a substantially constant current through the thermistor, which corresponds to the level of current present at the end of the constant-voltage mode. A voltage sensor measures the voltage drop across the thermistor during the constant-current mode, which varies according to fluid flow rate, and thereby provides a measurement of fluid flow rate.

In more detailed features of the invention, the driver circuit includes a transistor and a current-sensing resistor connected in series with the thermistor. When operating in the constant-voltage mode, the driver circuit conditions the transistor to conduct a current through the series-connected thermistor and current-sensing resistor, such that the voltage across the resistor is a measure of that current. Further, when operating in the constant-current mode, the driver circuit conditions the transistor to conduct a constant current through the current-sensing resistor, and thus through the thermistor, the current having a magnitude corresponding to the magnitude of the current conducted at the end of the constant-voltage mode.

In another more detailed feature of the invention, the driver circuit can further include a capacitor, which is charged during the constant-voltage mode to a voltage level corresponding to the voltage drop across the current-sensing resistor. Thereafter, when the driver circuit operates in the constant-current mode, the voltage level on the capacitor is maintained so as to condition the transistor to conduct an electrical current that provides a corresponding voltage drop across the current-sensing resistor. The driver circuit further can operate in an off mode, in which it applies substantially no current through the thermistor, and an electrical switch advantageously can be used to select between the constant-voltage mode, the constant-current mode, and the off mode.

Other features and advantages of the present invention should become apparent from the following description of the preferred embodiment, taken in conjunction with the accompanying drawings, which illustrate, by way of example, the principles of the invention.

DESCRIPTION OF THE PREFERRED EMBODIMENTS

Figure 1:
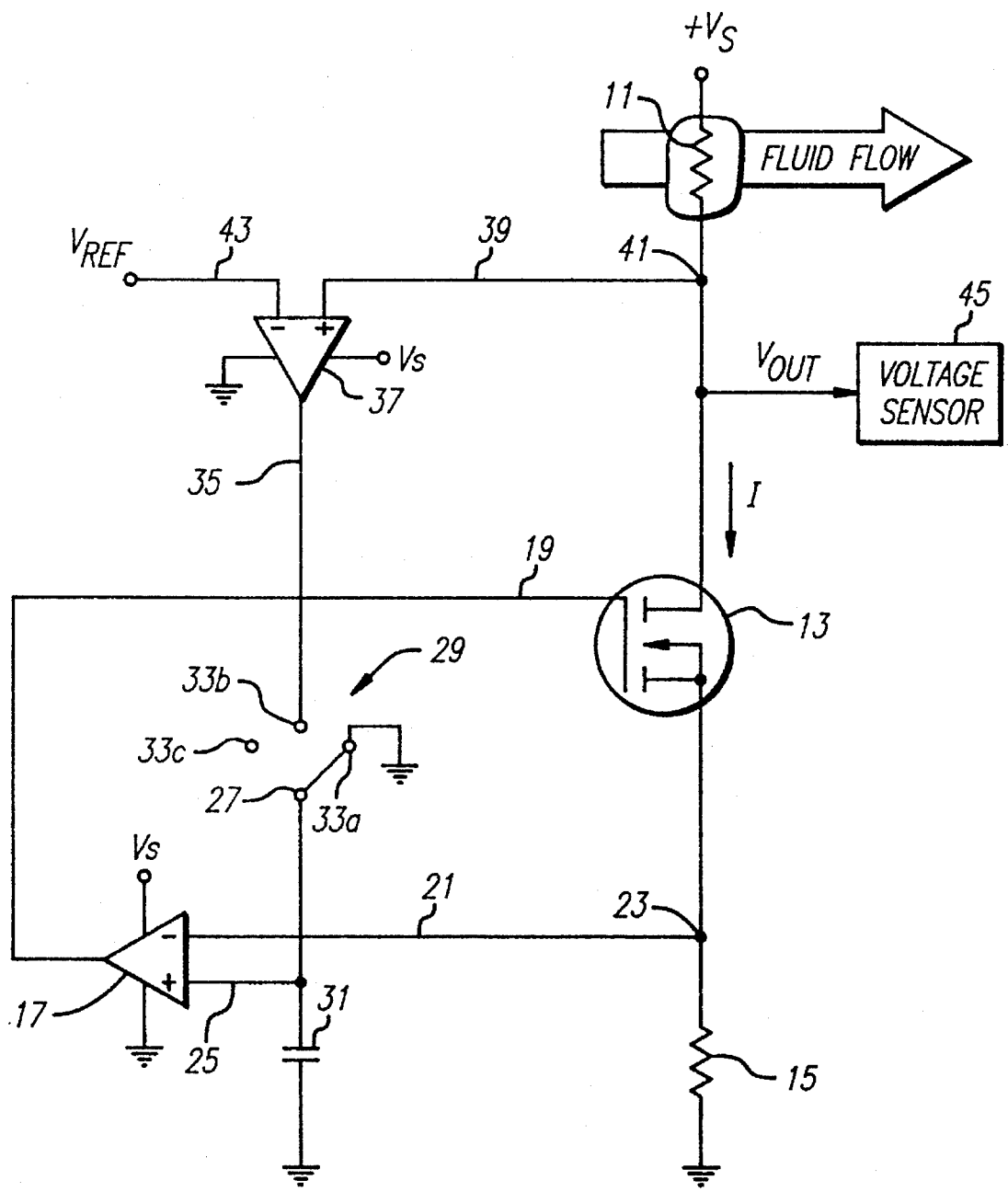
FIG. 1 is a schematic diagram of a blood flow rate measuring apparatus in accordance with the invention.

With reference now to the drawings, and particularly to FIG. 1, there is shown a blood flow rate measuring apparatus configured for use in conjunction with an implantable device such as a cardiac pacemaker (not shown). The apparatus measures blood flow rate using a thermistor 11 implantable within a patient's blood vessel and exposed to the flow of blood. The apparatus conducts a prescribed electrical current through the thermistor, causing the thermistor's temperature to rise, while the flow of blood past the thermistor carries away heat and thus reduces the rate of heating. The heating rate varies inversely with the blood's flow rate, being a maximum when the flow rate is zero. The apparatus measures the voltage drop across the thermistor to ascertain the blood's flow rate, and it does so in a way that minimizes the effect of any variations in ambient temperature, i.e., blood temperature.

More particularly, the thermistor 11, a metal-oxide silicon field-effect transistor (MOSFET) 13, and a current-sensing resistor 15 are connected in series between a positive voltage supply $V_S$ and ground. The MOSFET is controlled by an operational amplifier 17, whose output terminal is connected via line 19 to the MOSFET's gate terminal. The negative input terminal of the operational amplifier is connected via line 21 to the node 23 between the MOSFET's source terminal and the current-sensing resistor, and the positive input terminal of the operational amplifier is connected via line 25 to the common terminal 27 of a three-pole switch 29. In addition, a storage capacitor 31 is connected between that positive input terminal and ground.

The three-pole switch 29 includes a first pole 33a, a second pole 33b and a third pole 33c. The switch preferably is an electronic switch although, for simplicity, it is shown in FIG. 1 as a mechanical switch. The first pole 33a is connected directly to ground, the second pole 33b is connected via line 35 to the output terminal of a second operational amplifier 37, and the third pole 33c is an open circuit. The positive input terminal of the operational amplifier 37 is connected via line 39 to the node 41 between the thermistor 11 and the MOSFET's drain terminal, and the negative input terminal of the operational amplifier 37 is connected via line 43 to a voltage reference $V_{ref}$. $V_{ref}$ is a fixed voltage less than the supply voltage $V_S$. By way of example, if $V_S$ is 5.0 volts, $V_{ref}$ can be about 4.0 volts.

The driver circuit of FIG. 1 has three operating modes, which are selected by the three-pole switch 29. These modes include an initial off mode, a constant-voltage mode, and a constant-current mode.

In the off mode, which is selected when the switch 29 connects its common terminal 27 to the first, grounded pole 33a, zero volts is applied via line 25 to the positive input terminal of the operational amplifier 17. The operational amplifier 17 therefore couples an appropriate signal via line 19 to the gate terminal of the MOSFET 13, so as to bias the MOSFET off. Substantially zero electrical current therefore is conducted through the thermistor 11 during this initial off mode, and the thermistor's temperature will be in equilibrium with ambient temperature.

When it is desired to measure blood flow rate, the switch 29 is moved from the first, grounded pole 33a to the second pole 33b, which is connected via line 35 to the operational amplifier 37. This conditions the driver circuit to operate in its constant-voltage mode, in which it applies a substantially constant voltage across the thermistor 11. In particular, the MOSFET 13 is conditioned to conduct sufficient current through the thermistor to bring the voltage present at the node 41 between the thermistor and the MOSFET to a value equal to $V_{ref}$. In this constant-voltage mode, both operational amplifiers 17 and 37 operate in a linear fashion, with substantially equal voltages present at their respective positive and negative input terminals. Thus, the storage capacitor 31 connected to the positive input terminal of the operational amplifier 17 is automatically charged to a voltage level substantially equal to the voltage across the current-sensing resistor 15.

It will be appreciated that the current conducted through the thermistor 11 while a constant voltage (i.e., $V_S - V_{ref}$) is being applied across it will vary according to the thermistor's initial resistance, which as mentioned above varies with temperature. An accurate measure of this current, and thus the thermistor's initial temperature, is provided by the voltage drop across the current-sensing resistor 15. It is important that the constant-voltage mode have a time duration sufficient only to establish this initial current level and insufficient to cause any appreciable heating of the thermistor.

After a predetermined time duration, the circuit is conditioned to advance from its constant-voltage mode to its constant-current mode. In this constant-current mode, which is entered when the switch 29 is moved to the third, open pole 33c, the current conducted through the thermistor 11 is maintained at its level that existed at the end of the constant-voltage mode. This is achieved by maintaining the voltage on the storage capacitor 31, which corresponds to the voltage drop across the current-sensing resistor 15, and thus is a measure of the current that was being conducted through the thermistor at the end of the constant-voltage mode. The operational amplifier 17 thereupon outputs an appropriate control signal via line 19 to condition the MOSFET 13 to continue conducting that same electrical current through the current-sensing resistor, and thus through the thermistor.

Figure 2A:
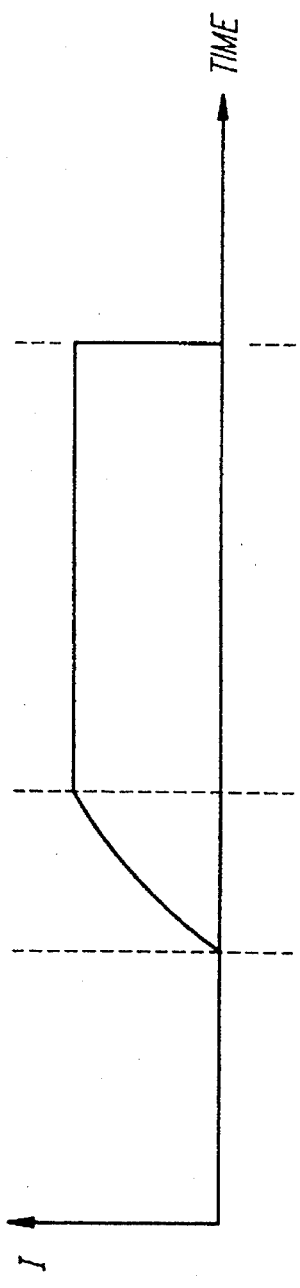
FIGS. 2(a) and (b) are timing diagrams of signals present in the blood flow rate measuring apparatus of FIG. 1.
Figure 2B:
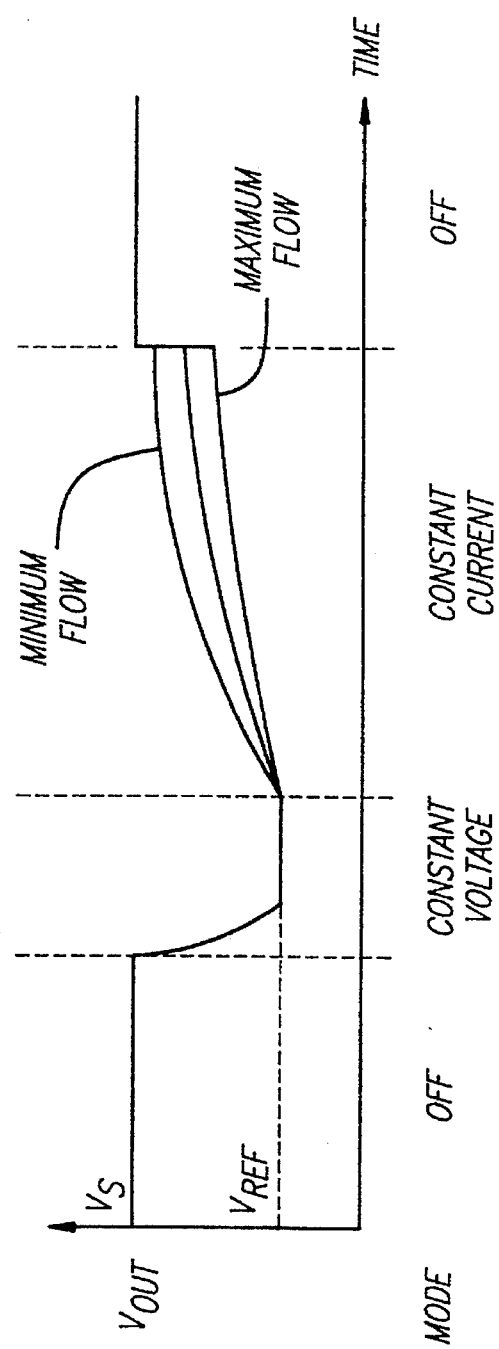

With a constant current being conducted through the thermistor 11, the thermistor's temperature will increase, with the rate of increase varying according to the rate at which the blood flowing past the thermistor carries heat energy away. Thus, the temperature will rise relatively more for a low flow rate and relatively less for a high flow rate. The thermistor preferably has a negative temperature coefficient, so the voltage drop across it will reduce relatively more for a low flow rate and relatively less for a high flow rate. This translates to a large increase in the voltage, $V_{out}$, present at the mode 41 for a low flow rate and a small increase in that voltage for a high flow rate. This is depicted in FIG. 2(b). A voltage sensor 45 monitors the voltage present at the node 41 at the end of the constant-current mode, and it compares this voltage with values stored in an appropriate look-up table, to produce a measurement of blood flow rate.

It will be appreciated that by conditioning the driver circuit first to apply a constant voltage across the thermistor 11, and subsequently to conduct a constant current through the thermistor, such current being selected to correspond to the maximum current conducted during the constant-voltage mode, the undesired effects of ambient temperature can be eliminated. Regardless of ambient temperature, the circuit will be conditioned to conduct a level of current through the thermistor that yields a voltage drop accurately representative of flow rate. If, for example, the ambient temperature is relatively high, a relatively low current will be developed through the thermistor at the end of the constant-voltage mode.

After the driver circuit has completed its blood flow rate measurement, at the end the constant-current mode, the circuit can be re-initialized to its off mode by returning the switch 29 to its condition where the common terminal 27 is connected via the first pole 33a to ground. Thereafter, after a sufficient time delay to allow the thermistor's temperature to return to ambient temperature, the measurement process can be repeated.

In an alternative embodiment, not shown in the drawings, the heating of the thermistor can be separated from the measurement of thermistor current. In this embodiment, the voltage on the storage capacitor is maintained constant even though current through the thermistor is cut off by an additional switch. By briefly driving the thermistor with a current pulse having a magnitude corresponding to that represented by the capacitor voltage, the resulting voltage drop across the thermistor can be measured without adding significant additional heat to the thermistor. This technique also can be used to measure cool-down of the thermistor after the heating cycle has been finished. Cool down is another measure of flow rate.

It should be appreciated from the foregoing description that the present invention provides an improved thermistor-based apparatus and method for measuring blood flow rate. In an initial constant-voltage mode, a driver circuit applies a constant-voltage across a thermistor exposed to a flow of blood, and in a subsequent constant-current mode, the driver circuit applies a constant current through the thermistor, the magnitude of that constant current corresponding to the current level at the end of the constant-voltage mode. A voltage sensor measures the resultant voltage drop across the thermistor, which is a direct measurement of blood flow rate and which is substantially insensitive to variations in ambient temperature.

Although the invention has been described in detail with reference only to the presently preferred embodiment, those skilled in the art will appreciate that various modifications can be made without departing from the invention. Accordingly, the invention is defined only by the following claims.

What is claimed is:

1. A fluid flow measuring apparatus comprising:
   a thermistor having an electrical resistance that varies with temperature, the thermistor being exposed to a flow of fluid;
   a driver circuit operable in an initial constant-voltage mode and a subsequent constant-current mode, wherein in the initial constant-voltage mode the driver circuit applies a prescribed substantially constant voltage across the thermistor, to produce an electrical current that varies according to the temperature of the thermistor, and wherein in the subsequent constant-current mode the driver circuit applies a substantially constant current through the thermistor that corresponds to the current conducted at the end of the constant-voltage mode, wherein the resulting change in voltage across the thermistor is indicative of the fluid flow rate; and
   a voltage sensor that measures the voltage across thermistor during the constant-current mode and thereby determines fluid flow rate.

2. A fluid flow measuring apparatus as defined in claim 1, wherein:
   the driver circuit includes a transistor and a current-sensing resistor connected in series with the thermistor;
   the driver circuit, when operating in the constant-voltage mode, directs the current through the series-connected transistor and current-sensing resistor, such that the voltage across the current-sensing resistor is a measure of the current; and
   the driver circuit, when operating in the constant-current mode, conditions the transistor to conduct a substantially constant current through the current-sensing resistor, and thus through the thermistor, having a magnitude that corresponds to the magnitude of the current conducted at the end of the constant-voltage mode.

3. A fluid flow measuring apparatus as defined in claim 2, wherein:
   the driver circuit further includes a capacitor;
   the driver circuit, in the constant-voltage mode, charges the capacitor to a voltage level corresponding to the voltage across the current-sensing resistor; and
   the driver circuit, in the constant-current mode, maintains the voltage level on the capacitor and conditions the transistor to conduct an electrical current that provides a corresponding voltage drop across the current-sensing resistor.

4. The fluid flow measuring apparatus as defined in claim 3, wherein the driver circuit further includes a switch that selects between the constant-voltage mode and the constant-current mode.

5. The fluid flow measuring apparatus as defined in claim 1, wherein the driver circuit further is operable in an off mode in which it applies substantially no electrical current through the thermistor.

6. Apparatus associated with a device implantable in a patient, for measuring blood flow rate, comprising:
   a thermistor having an electrical resistance that varies with temperature, the thermistor being disposed within a blood vessel and exposed to a flow of blood;
   a driver circuit operable in an initial constant-voltage mode and a subsequent constant-current mode, wherein in the initial constant-voltage mode the driver circuit applies a prescribed substantially constant voltage across the thermistor, to produce an electrical current that varies according to the temperature of the thermistor, and wherein in the subsequent constant-current mode the driver circuit applies a substantially constant current through the thermistor that corresponds to the current conducted at the end of the constant-voltage mode, wherein the resulting change in voltage across the thermistor is indicative of the blood flow rate; and
   a voltage sensor that measures the voltage across the thermistor during the constant-current mode and determines the blood's flow rate.

7. Apparatus as defined in claim 6, wherein:
   the driver circuit includes a transistor and a current-sensing resistor connected in series with the thermistor;
   the driver circuit, when operating in the constant-voltage mode, directs the current through the series-connected transistor and current-sensing resistor, such that the voltage across the current-sensing resistor is a measure of the current; and
   the driver circuit, when operating in the constant-current mode, conditions the transistor to conduct a substantially constant current through the current-sensing resistor, and thus through the thermistor, having a magnitude that corresponds to the magnitude of the current conducted at the end of the constant-voltage mode.

8. Apparatus as defined in claim 7, wherein:
   the driver circuit further includes a capacitor;
   the driver circuit, in the constant-voltage mode, charges the capacitor to a voltage level corresponding to the voltage across the current-sensing resistor; and
   the driver circuit, in the constant-current mode, maintains the voltage level on the capacitor and conditions the transistor to conduct an electrical current that provides a corresponding voltage drop across the current-sensing resistor.

9. Apparatus as defined in claim 8, wherein the driver circuit further includes a switch that selects between the constant-voltage mode and the constant-current mode.

10. Apparatus as defined in claim 6, wherein the driver circuit further is operable in an off mode in which it applies substantially no electrical current through the thermistor.

11. A method for use in a device implantable in a patient, for measuring blood flow rate, comprising:
    implanting a thermistor in a blood vessel of a patient, in a position where it is exposed to a flow of blood, the thermistor having an electrical resistance that varies with temperature;
    applying a substantially constant voltage across the thermistor for a first time interval, to produce an electrical current that varies according to the temperature of the thermistor;
    subsequently conducting a predetermined current through the thermistor for a second time interval, such current corresponding to the current conducted at the end of the first time interval; and measuring the voltage drop across the thermistor at the end of the second time interval, to determine blood flow rate.

12. A method as defined in claim 11, and further comprising:

conducting the predetermined current through the thermistor for a third time interval; and measuring the voltage drop across the thermistor at the end of the third time interval, to further determine blood flow rate.

* * * * *